(12) United States Patent
Edge et al.

(10) Patent No.: US 9,265,933 B2
(45) Date of Patent: Feb. 23, 2016

(54) COCHLEAR IMPLANTS CONTAINING BIOLOGICAL CELLS AND USES THEREOF

(75) Inventors: Albert Edge, Newton, MA (US); Stefan Heller, Menlo Park, CA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 1628 days.

(21) Appl. No.: 11/518,099

(22) Filed: Sep. 8, 2006

(65) Prior Publication Data

US 2007/0093878 A1    Apr. 26, 2007

Related U.S. Application Data

(60) Provisional application No. 60/715,080, filed on Sep. 8, 2005.

(51) Int. Cl.
*A61N 1/05* (2006.01)
*A61L 27/36* (2006.01)
*A61L 27/38* (2006.01)
(Continued)

(52) U.S. Cl.
CPC ........... *A61N 1/0541* (2013.01); *A61L 27/3633* (2013.01); *A61L 27/3834* (2013.01); *A61L 27/54* (2013.01); *A61L 2300/414* (2013.01);
(Continued)

(58) Field of Classification Search
CPC .. A61N 1/0541; A61N 1/326; A61N 1/36121
USPC ............................................................ 607/57
See application file for complete search history.

(56) References Cited

U.S. PATENT DOCUMENTS

| 4,408,608 | A | * | 10/1983 | Daly et al. | 607/57 |
| 4,532,930 | A | * | 8/1985 | Crosby et al. | 607/57 |

(Continued)

FOREIGN PATENT DOCUMENTS

| WO | WO 98/00014 | 1/1998 |
| WO | WO 99/06064 | 2/1999 |

(Continued)

OTHER PUBLICATIONS

Yagi et al. A Computational Study on a Electrode Array in a Hybrid Retinal Implant. Proc 1998 IEEE Int. Joint Conf. Neural Networks. (1998); 780-783.*

(Continued)

*Primary Examiner* — Theodore Stigell
*Assistant Examiner* — Jeremiah Kimball
(74) *Attorney, Agent, or Firm* — Fish & Richardson P.C.

(57) ABSTRACT

The present invention features devices for treating hearing loss, methods of making the devices, and methods for treating hearing loss. The devices include cochlear implants with biological cells placed at least on one or more of the electrodes of the implant. The cochlear implants then bypass dead or damaged hair cells in the cochlea by directly stimulating the auditory nerve fibers leading to the perceptions of sound. The biological cells can extend processes from the implant to the brainstem, creating a bridge that transmits electric signals from the electrode to the brainstem more efficiently than traditional cochlear implants. Methods of making the implants include applying a composition containing biological cells to an electrode of a cochlear implant, and treatment methods include implanting a cochlear implant that carries biological cells on one or more electrodes into a human who has experienced profound hearing loss (e.g., sensorineural hearing loss).

26 Claims, 3 Drawing Sheets

(51) Int. Cl.
  *A61L 27/54* (2006.01)
  *A61N 1/36* (2006.01)
  *A61N 1/32* (2006.01)

(52) U.S. Cl.
  CPC ............. *A61L2430/14* (2013.01); *A61N 1/326* (2013.01); *A61N 1/36032* (2013.01); *A61N 1/36121* (2013.01)

(56) References Cited

U.S. PATENT DOCUMENTS

| | | | |
|---|---|---|---|
| 6,038,484 A | 3/2000 | Kuzma et al. | |
| 6,171,610 B1 | 1/2001 | Vacanti et al. | |
| 6,304,787 B1 | 10/2001 | Kuzma et al. | |
| 6,309,410 B1 | 10/2001 | Kuzma et al. | |
| 6,429,191 B1 * | 8/2002 | Gao | 514/2 |
| 6,654,729 B1 * | 11/2003 | Hickman et al. | 706/15 |
| 6,778,858 B1 | 8/2004 | Peeters | |
| 2004/0122475 A1 | 6/2004 | Myrick et al. | |

FOREIGN PATENT DOCUMENTS

| | | | | |
|---|---|---|---|---|
| WO | WO 00/27426 | 5/2000 | | |
| WO | WO 02/20087 | 3/2002 | | |
| WO | WO 02/41666 | 5/2002 | | |
| WO | WO 03/034960 | 5/2003 | | |
| WO | WO 03/072193 | 9/2003 | | |
| WO | WO 2004/050056 | 6/2004 | | |
| WO | WO 2004050056 A1 * | 6/2004 | | A61K 9/00 |

OTHER PUBLICATIONS

Parker et al. The Potential Use of Stem Cells for Cochlear Repair. Audiology & Neuro-Otology. (2004); vol. 9, No. 2; 72-80.*

Ito et al. A Study on Culturing of Neurons on Micro-Electrode Array in Hybrid Retinal Implant. Proc. 6th Int. Conf. on Neural Info. Processing (ICONIP). (1999); 381-385.*

Schmidt et al. Neural Tissue Engineering: Strategies for Repair and Regeneration. Annu. Rev. Biomed. Eng. (2003). 5:293-347.*

Eddington et al. Cochlear Implants—Restoring Hearing to the Deaf. On The Brain. (1994). vol. 3, No. 4.*

Li et al. Generation of hair cells by stepwise differentiation of embryonic stem cells. Proc Natl Acad Sci USA. Nov. 11, 2003;100(23):13495-500.*

Ying et al. Conversion of embryonic stem cells into neuroectodermal precursors in adherent monoculture. Nature Biotechnology. (2003) 21:183-186.*

Donaldson et al., "Recruitment by motor nerve root stimulators: significance for implant design," Med. Eng. Phys., 25(7):527-537 (2003).

Eddington and Pierschella, "Cochlear Implants—Restoring Hearing to the Deaf," On the Brain, vol. 3, No. 4 (Fall 1994), downloaded from http://www.med.harvard.edu/publications/On_The_Brain/Volume03/Number4/Cochlear.html.

George et al., "Fabrication and biocompatibility of polypyrrole implants suitable for neural prosthetics," Biomaterials, 26(17):3511-3519 (2005).

Lee and Chao, "Activation of Trk neurotrophin receptors in the absence of neurotrophins," Proc. Natl. Acad. Sci. U.S.A., 98(6):3555-60 (2001), Epub. Mar 6, 2001.

Lee et al., "Efficient generation of midbrain and hindbrain neurons from mouse embryonic stem cells," Nat. Biotechnol., 18(6):675-679 (2000).

Maher et al., "The neurochip: a new multielectrode device for stimulating and recording from cultured neurons," J. Neurosci. Methods, 87(1):45-56 (1999).

Palanker et al., "Migration of retinal cells through a perforated membrane: implications for a high-resolution prosthesis," Invest. Ophthalmol. Vis. Sci., 45(9):3266-3270 (2004).

Ruiz et al., "Treatment with TRK C Agonist Antibodies Delays Disease Progression in Neuromuscular Degeneration (nmd) Mice," Hum. Mol. Gen. 14(13):1825-1837 (2005).

* cited by examiner

COCHLEAR IMPLANTS CONTAINING BIOLOGICAL CELLS AND USES THEREOF

RELATED APPLICATIONS

This application claims the benefit of U.S. Provisional Application No. 60/715,080, filed Sep. 8, 2005, which is incorporated herein by reference in its entirety.

TECHNICAL FIELD

This invention generally relates to cochlear implants containing biological cells and methods of making and using the cochlear implants.

BACKGROUND

A cochlear implant is an electronic device that is implanted into the inner ear to restore auditory perception, at least partially, to the deaf and hard-of-hearing. Cochlear implants create auditory sensation by generating electric field gradients in the area of the peripheral nerve fibers of the auditory nerve bundle. This bundle contains approximately 30,000 individual afferent nerve fibers normally linked to approximately 4,500 inner hair cells. Sound signals are picked up by a microphone within the implant, converted into digital signals, and processed by a signal processor in order to activate different stimulation channels. These channels, in turn, stimulate different groups of nerve fibers within the auditory nerve.

Figure 1:
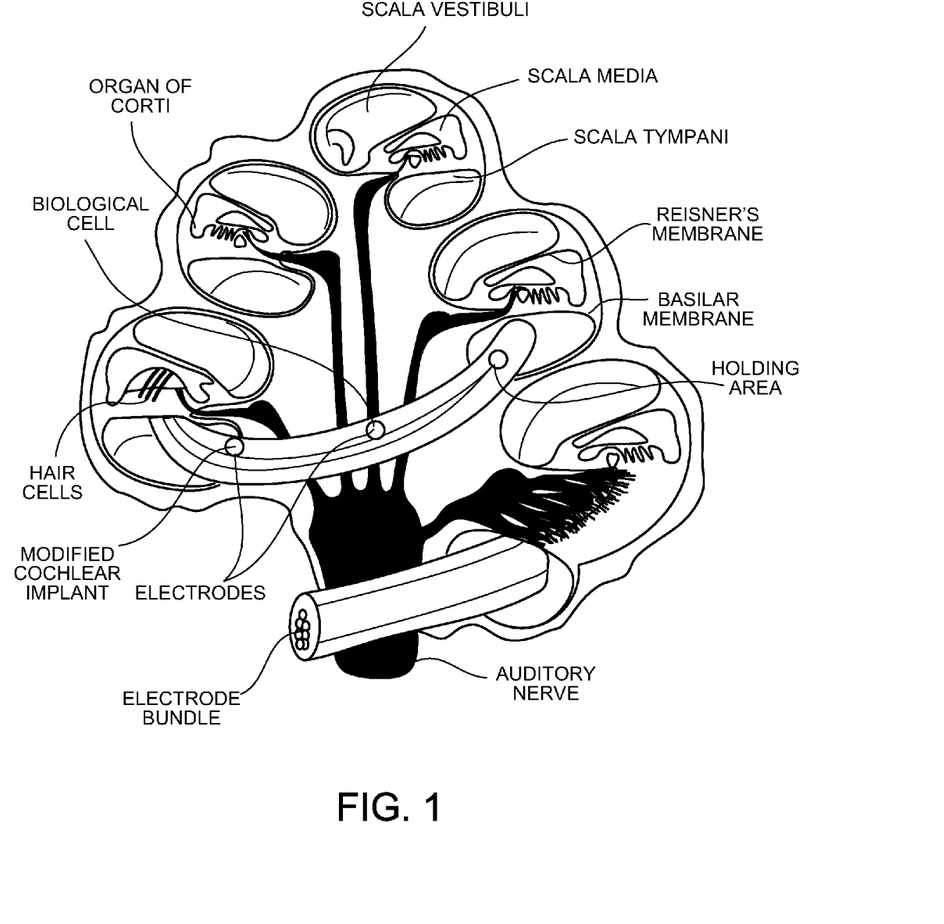
FIG. 1 is a diagram illustrating a cochlear implant (shown in black) positioned within a patient, bypassing the normal pathways of the ear canal and the three bones of the middle ear (Eddington and Pierschalla, "Cochlear Implants: Restoring Hearing to the Deaf," *On the Brain* (The Harvard Mahoney Neuroscience Institute Letter) Vol. 3, No. 4, Fall 1994).
Figure 2:
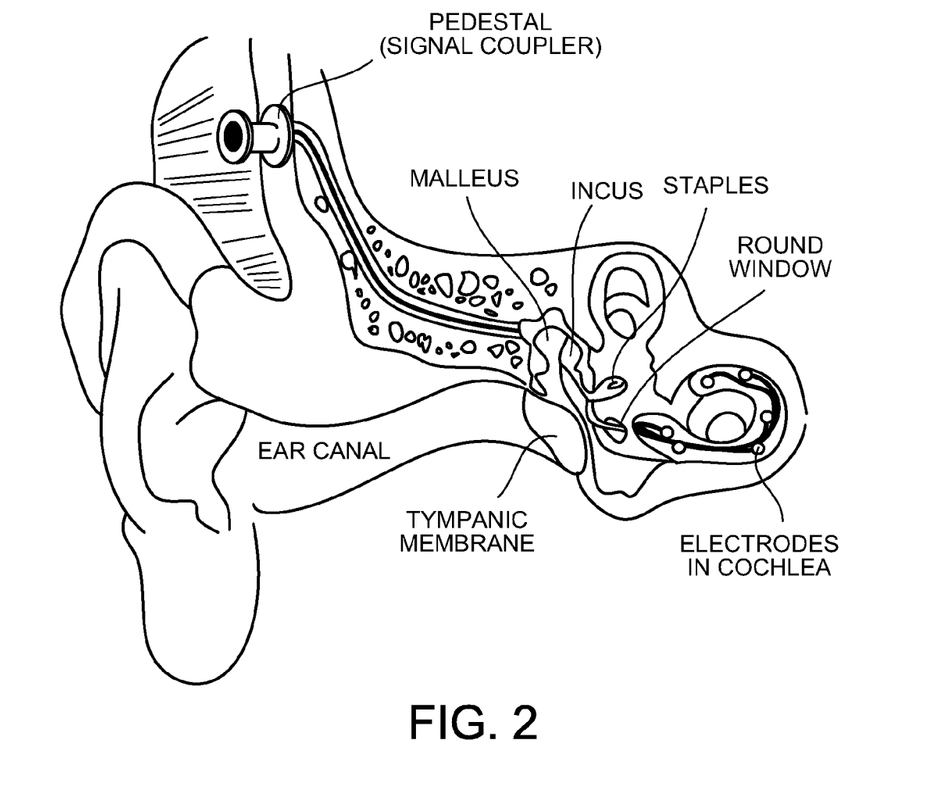
FIG. 2 is a diagram of an implanted cochlea. The electrodes are positioned to activate the auditory nerve fibers (Eddington and Pierschalla, "Cochlear Implants: Restoring Hearing to the Deaf," *On the Brain* (The Harvard Mahoney Neuroscience Institute Letter) Vol. 3, No. 4, Fall 1994).

The ear is composed of four main sections: the external ear, middle ear, inner ear, and the transmission pathway to the hearing center in the brain. In normal hearing, sound waves travel along the external ear canal and cause the tympanic membrane (also called the ear drum) to vibrate. The three small bones of the middle ear (the malleus, incus, and stapes) transmit these vibrations to the cochlea of the inner ear. The cochlea is divided along its length by a basilar membrane that distributes vibrational energy longitudinally by frequency. The lowest frequencies cause maximum membrane motion near the cochlea's apex, and the highest frequencies maximize motion near the base. Four parallel rows of hair cells extend along the length of the basilar membrane and, when vibrated, transduce acoustic signals into electrical impulses carried to the brain by auditory nerve fibers (see FIGS. 1 and 2).

SUMMARY

The present invention features devices for treating hearing loss, methods of making the devices, and methods for treating hearing loss. The devices include cochlear implants with biological cells placed at least on one or more of the electrodes of the implant. While cochlear implants are described further below, we note here that they include electrodes that bypass dead or damaged hair cells in the cochlea by directly stimulating the auditory nerve fibers leading to the perceptions of sound. The cells can extend processes from the implant to the brainstem, creating a bridge that transmits electric signals from the electrode to the brainstem more efficiently than traditional cochlear implants. Methods of making the implants include applying a composition containing biological cells to an electrode of the implant, and treatment methods include implanting a cochlear implant that carries cells on one or more electrodes into a human who has experienced hearing loss (e.g., sensorineural hearing loss).

In one aspect, the invention features a cochlear implant that carries a biological cell that is operably associated with an electrode within the implant. The biological cell can be, for example, a stem cell, a neural progenitor cell, or a neuron. The neural progenitor cell or neuron can be derived from a stem cell or from a more differentiated progenitor cell. The biological cell can be embedded in a composition that covers the electrodes, fully or partially. A neuron can be an afferent neuron (i.e., a neuron having neural processes that extend towards the central nervous system). For example, processes from an afferent neuron can extend toward the brainstem and synapse with neurons there. In addition to, or instead of, mature neurons, the composition can also include stem cells or stem-cell derived neural progenitor cells, which are not completely differentiated, but which express some genes that are typically or exclusively expressed in neurons. The stem cells are pluripotent, undifferentiated, and capable of differentiating into a variety of different cell types. As these cells differentiate into neurons, they can supplement any previously present neurons and may therefore replace neurons if they degenerate within the implant. The composition in which the cells (e.g., stem cells, progenitor neural cells and differentiated neural cells) are contained can include a component of the extracellular matrix (ECM), including one or more of fibronectin, laminin, collagen, elastin, vitronectin, a proteoglycan, a glycosaminoglycan, and the like. The composition in contact with the electrodes, or otherwise positioned with the device to transduce acoustic signals, can also include a neurotrophin, such as nerve growth factor (NGF), brain-derived neurotrophic factor (BDNF), neurotrophin-3 (NT-3), ciliary neurotrophic factor (CNTF), neurotrophin-4/5 (NT-4/5), glial-cell line derived neurotrophic factor (GDNF), leukemia inhibitory factor (LIF), or fibroblast growth factor (FGF). More generally, the neurotrophin can be any compound or substance that stimulates neural cell survival or differentiation, which may manifest as process outgrowth and which may be mediated by the interaction with cellular receptors (e.g., tyrosine receptor kinase C (trkC), tyrosine receptor kinase B (trkB)).

A cochlear implant carrying biological cells on its electrodes can also have a separate holding area containing stem cells or progenitor neural cells located near the electrodes. These cells can differentiate to replace the degenerated neurons of the human implantee or to replace neural cells (including neurons and progenitor neural cells) of the implant, should they degenerate. This store of cells can also include undifferentiated stem cells and neurons (e.g., afferent neurons). The holding area can consist of one or more dimples or grooves on the implant, such as on the region of the implant between the implanted stimulator/receiver unit and the electrode bundle, and nearer the electrode bundle.

In another aspect, methods of making a cochlear implant are provided. These methods include the step of applying a cell (e.g., a stem cell, a more differentiated stem cell-derived progenitor, or a recognizable neural cell) to one or more of the structures within the implant (e.g., the electrodes of the cochlear implant). The composition applied can further include a component of the ECM (as noted above, suitable components include fibronectin, laminin, collagen, elastin, vitronectin, a proteoglycan, a glycosaminoglycan, and the like). The composition can also include a neurotrophin, such as one or more of NGF, BDNF, NT-3, CNTF, NT-4/5, GDNF, LIF, and FGF.

The cells applied to the implant can be associated with a hydrogel or other porous matrix. Suitable and commercially available hydrogels include MATRIGEL™ (BD Biosciences, San Jose, Calif.) and ECM GEL (Sigma, St. Louis, Mo.). A hydrogel is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions, cross-linking, or similar means. While the properties of the hydrogel or other porous matrix can vary, they will typically be of a uniform density and, therefore, allow a uniform distribution of cells. The hydrogel or matrix can contain varying numbers of cells (e.g., about 1-100 million cells per ml). The nature of the hydrogel or matrix allows diffusion of nutrients, neurotrophins, cellular metabolites, and the like, to and from the implant and thereby facilitates the survival and/or differentiation of the cells within. Where a hydrogel is used, it can include one or more of a polysaccharide, a protein, a polyphosphazene, a poly(oxyethylene)-poly oxypropylene) block polymer, a poly(oxyethylene)-poly(oxypropylene) block polymer of ethylene diamine, a polyacrylic acid, a poly(methacrylic acid) a copolymer of acrylic acid and methacrylic acid, poly(vinyl acetate), or a sulfonated polymer. The composition can alternatively be a porous matrix that is not a hydrogel. The porous matrix can be, or can include, a sponge, a foam, a calcium carbonate matrix (e.g., coral or hydroxyapatite), or a rigid inorganic ceramic, or metal structure having internal pores (e.g., a honeycomb). For example, the matrix can be made from titanium, or can be a skeleton or mesh of fine struts and/or thick struts. The fine struts can include thin interwoven polymer fibers and the thick struts can be a network of metal, inorganic, ceramic, or plastic rods. Where a polymer is used, it can be a polymer of polylactic acid (PLA), polyglycolic acid (PGA), or a copolymer thereof (PLGA). We may refer to the hydrogel and the other porous matrices as support structures.

ECM components and growth factors, such as a neurotrophin (e.g., NT-3) can be included in the device and may be embedded in the matrix or immobilized on the matrix. The porous matrix can support cell chemotaxis. A hydrogel or porous matrix used with a cochlear implant is biocompatible (e.g., non-toxic to cells).

An optional step in making a cochlear implant featured in the invention includes applying a separate concentrated store of stem-cell-derived neural progenitor cells or neurons near the electrodes, such as in dimples or grooves etched into the implant. This holding area may also be a lumen or another attached reservoir for storing the cells. The cells in this separate holding area can be embedded in a composition including extracellular matrix proteins, and optionally, neurotrophins, as described above. Undifferentiated stem cells, and differentiated neurons can also be stored in this separate holding area.

One aspect featured in the invention includes a modified cochlear implant for use in the treatment of a hearing loss. The modified cochlear implant can include any implant described herein, including implants having biological cells placed at least on one or more electrodes of the implant.

In one aspect, the invention features a method of treating a human by implanting a cochlear implant carrying cells into the human. The cochlear implant can be implanted into the scala tympani of the ear, or the device can be implanted outside of the cochlea, such as in the middle ear, or in the inner ear, and near the auditory nerve. The treatment methods can include a step of identifying a human in need of treatment, such as identifying a human whose hearing does not improve following use of an external hearing aid. A human who is a candidate for treatment with a cochlear implant carrying cells can have unilateral or bilateral hearing loss, and/or severe or profound hearing loss. The human can be a child, typically having an age of from between about 12 months and 18 years, or the human can be an adult over the age of 18 years. Following treatment with a cochlear implant featured in the invention, the human can follow a rehabilitation regimen, where the implantee builds skills, including hearing, speech and language skills. The rehabilitation regimen can be maintained for 6 months, one year, or longer than a year. The human can attend rehabilitation sessions more frequently in the months immediately following implantation of the device and less frequently as skill levels become more advanced.

The treatment methods featured in the invention can include implanting biological cells into the inner ear of the human, in addition to the implantation of the modified cochlear implant, which has a composition on the electrodes that includes biological cells. These supplemental biological cells implanted into the inner ear of the modified cochlear implant recipient can be any of the biological cells described above, which are also suitable for use on the modified cochlear implant. For example, the supplemental implanted cells can include stem cells, neural progenitor cells, or neurons, or a combination of these cell-types. Supplemental progenitor cells or neurons can be derived from a stem cell or from a more differentiated progenitor cell. The supplemental biological cells can be implanted into the inner ear, such as near the base of the auditory nerve near its connection with the cochlea. The cells can alternatively be implanted into the modiolus of the cochlea. The supplemental cells can extend processes towards the auditory nerve, as well as towards the cochlear implant to provide additional connections between the implant and the auditory nerves, thereby providing additional neural connections which can further increase the efficiency of the transmission of electric signals from the electrodes of the implant to the brainstem. There may be certain advantages to the use of cochlear implants that include cells. For example, traditional cochlear implants (i.e., implants that do not include cells) do not form connections with the auditory nerve, and so the electrical stimulation emanating from the implant must travel through extracellular fluid, connective tissue and myelinated tissue to reach the auditory nerve cells. The distance the electrical stimulation has to travel to reach the auditory nerve cells and the electrical resistance of these obstacles weakens the effect of the electrical stimulation. Providing neural cells to the implant, however, can generate a bridge between the implant and the auditory nerves (e.g., the spiral ganglion neurons) as the processes of the neural cells grow outwards to form synaptic connections with the auditory nerve. Alternatively, the neural cells of the implant can functionally replace the auditory neurons (e.g., the spiral ganglion neurons).

Other features and advantages of the invention will be apparent from the accompanying description and the claims. The contents of all references, pending patent applications and published patents, cited throughout this application are hereby expressly incorporated by reference. In case of conflict, the present specification, including definitions, will control.

DETAILED DESCRIPTION

We now further describe devices and methods for treating deafness and hearing loss in a human. The device can be a cochlear implant that has been modified by inclusion of cells, and the methods include implantation of such a device.

Cochlear Implants. A cochlear implant is an electronic device that is used to improve hearing in humans who have experienced hearing loss, particularly severe to profound hearing loss. These devices typically include an "external" and an "internal" part. The external part includes a microphone, which can be placed behind the ear, that detects sounds in the environment. The sounds are then digitized and processed by a small computer called a speech processor. The external components may be referred to as a processor unit. In addition to the microphone and speech processor, the external portion of the implant can include a power source, such as a battery and an external antenna transmitter coil. The internal part is an electronic device that is put under the skin in the vicinity of the ear and is commonly referred to as a stimulator/receiver unit (see FIG. 1). The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with the implanted antenna receiver coil provided with the stimulator/receiver unit. The communication is typically provided by a radio frequency (RF) link, but other such links have been proposed and implemented with varying degrees of success.

The implanted stimulator/receiver unit typically includes the antenna receiver coil that receives the coded signal and power from the external processor component, and a stimulator that processes the coded signal and outputs a stimulation signal to an electrode assembly, which applies the electrical stimulation directly to the auditory nerve producing a hearing sensation corresponding to the original detected sound.

An electrode connected to the electronic device is inserted into the inner ear. The electrode can be a bundle of wires that have open contacts spread along the length of the cochlea and represent different frequencies of sounds. The number of electrodes can vary from 1 to about 30 electrodes, such as about 5, 10, 15, 18, 20, 22, 24, 26, or 28 electrodes.

The biological cells described herein can be applied to any cochlear implant, regardless of the number of electrodes employed, the size of the speech processor, or other variations. The external components of the cochlear implant can be carried on the body of the implantee, such as in a pocket of the implantee's clothing, a belt pouch or in a harness, while the microphone can be attached to a clip and mounted behind the ear or attached to a piece of clothing, such as a lapel. Alternatively, the external components can be housed in a smaller unit capable of being worn behind the ear. Such a unit can house the microphone, power unit and the speech processor.

In yet another alternative, the components that are traditionally housed externally may be reduced in size to be implanted or worn in the ear (or a combination of both), resembling a hearing aid. For example, the battery and microphone may be housed in a unit worn in the ear, while the speech processor is implanted behind the ear.

Functionally, cochlear implants attempt to mimic the hair cells of the cochlea. Hair cells are the sensory cells that convert sound-derived mechanical stimulation into electrical signals that are relayed to the brain via auditory ganglion nerve cells (also called auditory neurons). Like hair cells, cochlear implants stimulate auditory neurons. This stimulation is typically achieved by surgically introducing the electrodes of the cochlear implant into the scala tympani of the cochlear spiral. An electronic device connected to the electrodes converts sound into impulses of different frequencies that stimulate the auditory neurons. The electrical stimulation has to travel through extracellular fluid, connective tissue and myelinated tissue to reach the auditory neurons, and the resistance created by these obstacles decreases the effect of the electrical stimulation. The inclusion of cells within the implant, however, as described herein, can create a direct physical connection between the implant and the patient's nervous system as the processes of the neural cells grow outwards to form synaptic connections with the auditory nerves, therefore enhancing stimulation of the auditory nerve, or to functionally replace one or more auditory neurons.

The biological cells can be operably associated with (e.g., attached to) a surface of the implant. A biological cell is operably associated with a cochlear implant when the cell, following implantation into a patient, transmits an electrical signal from the implant (e.g., from an electrode within the implant) to a cell within the patient's nervous system (e.g., to a cell within the auditory nerve) and thereby improves the patient's hearing. For example, the cells can be attached to a surface of the electrode bundle or to one or more of the electrodes themselves. In the latter case, neurites will extend from the cells through openings in any casing that may surround the electrode bundle. As described further below, the cells can be applied in a composition that may include one or more of a tissue culture medium (some of which may remain associated with the cells as they are moved from a tissue culture or storage vial), a polymer or gel, or a bio-active compound such as ECM protein or a growth factor. Alternatively, or in addition, one or more of these agents can be applied to the outside of the electrode bundle, over the electrodes themselves, or both as appropriate. The bioactive compounds support cell survival and may promote neurite outgrowth. Accordingly, a bioactive compound is one that upon inclusion in a modified cochlear implant, improves cell survival and/or neurite outgrowth relative to what would occur in the compound's absence.

The modified cochlear implant described herein can be implanted in any way traditional, unmodified implants are implanted (e.g., into the scala tympani). Alternatively, the modified implant can be positioned outside the cochlea, but in close vicinity to the auditory nerve (e.g., near enough that cells associated with the modified implant can form functional connections with the patient's auditory nerve fibers or other parts of the auditory nervous system). For example, if the auditory nerve is degenerated (e.g., due to trauma or genetic disorder), the implant can be positioned near the pathway of the lost auditory nerve fibers.

More specifically, cells attached to the implant will grow processes having the signal-transmitting properties of neurites. The processes will extend from the matrix coating the electrode (where applied or when present), or other area of the implant, and synapse with fibers within the auditory nerve. Alternatively, or in addition, the processes can extend along the pathway where the auditory nerve was located before fibers within it degenerated, and into the auditory brainstem. The neurites can synapse with endogenous auditory nerve fibers or with auditory neuron cell bodies. Neurites that extend to the auditory brain stem can connect with appropriate target cells in a way that sound perception is at least partially restored. Target cells, for example, include cells of the cochlear nucleus and other neurons along the central auditory pathways. For example, the neurites can connect with postsynaptic neurons in the cochlear nucleus, or can extend along the central auditory pathways to connect with neurons in the superior olivary nuclei; the nuclei of the lateral lemniscus, inferior colliculus, or medical geniculate nucleus; or the neurites can extend into the auditory cortex. The cell bodies that are initially positioned on the modified cochlear implant may remain on the implant or may migrate along the nerve fibers to form a structure that functionally replaces or supplements the auditory ganglion.

As described further below, the modified cochlear implant can include one or more cell types, including stem cells, neural cell progenitor cells, which may be derived from stem cells, and mature neurons. Progenitor cells are cells that are not fully differentiated. They can be derived from stem cells, which are pluripotent, and can be induced to differentiate into a variety of cell types. Stem cells or progenitor cells can be positioned within the modified implant (e.g., along the electrodes) with differentiated neural cells, and the stem cells or progenitor cells may also be included in a holding area in close vicinity to the electrodes. This store will replace cells that have degenerated in the ear and will also supplement the neural cells that form processes that synapse with auditory neurons and the auditory brainstem. Some of the stem cell-derived progenitor neural cells may remain in the modified cochlear implant, and some of the progenitor cells may migrate out of the device, either remaining quiescent or differentiating into additional neurons that connect the implant's electrodes with either the brainstem or with the remaining auditory neurons.

The modified cochlear implants can include a polymer, which may be within a hydrogel, or another porous substance. Extracellular matrix (ECM) proteins can be included in the composition, which may contain fibronectin and laminin, as well as collagens, proteoglycans, glycosaminoglycans, elastin, vitronectin and the like. The extracellular matrix component can include a matrigel, which is composed of collagen type IV, laminin, and heparan sulphate. The gelation of an ECM component can be carried out in the usual manner. For example, if the ECM component is collagen, then a collagen gel can be obtained by incubating an aqueous solution of 0.3-0.5% collagen at 37° C. for 10-20 minutes. If necessary, a gelling agent may be used in gelation of an ECM component. The gel matrix can include gelatin or agarose or any natural or synthetic extracellular proteinous matrix or basal membrane mimic including, but not limited to MATRIGEL™ (BD Biosciences, San Jose, Calif.), or ECM GEL, (Sigma, St. Louis, Mo.), or other hydrogels containing certain factors such as cytokines (e.g., growth factors and chemokines), antibodies, or other ligands for cell surface receptors. Preferably, the gel has a substantially high water content (e.g., water content of 60%, 65%, 70%, 75%, 80%, 85%, 90%, 91%, 92%, 93%, 94%, 95%, 96%, 97%, 98%, or 99%) and is porous enough to allow cell chemotaxis. Alternatively, the polymer can be a porous matrix exclusive of a hydrogel.

The gel or polymer mix can contain other factors that support neural cell growth and survival such as one or more neurotrophins. Neurotrophins are molecules that support the survival of different classes of neurons and include NT-3, BDNF, GDNF, NGF, CNTF, NT-4/5, LIF, and FGF. For example, neurotrophin NT-3 can be present in the polymer or gel where it interacts with a receptor, such as the trkC receptor, on the neural cells. Activation of the trkC receptor can promote neural cell outgrowth and survival. In another example, NT-4/5 can be present in the polymer or gel where it interacts with a receptor, such as the trkB receptor, to support cell growth and survival. Other molecules that can agonize or antagonize the receptors, or act as mimics of neurotrophins or other chemoattractant agents, can be included in the polymer or gel. Agonists of the receptors can, for example, provide trophic support to the co-grafted neurons. These can include antibodies, peptides, nucleic acids, and small molecule chemical compounds. For example, monoclonal antibody Mab2256 can be included in a polymer or matrix to agonize the trkC receptor (Ruiz et al., *Hum. Mol. Genet.* 14:1825-1837, 2005, E-published May 1, 2005). In another example, the small molecule beta-turn peptidomimetic D3 can be included in a polymer or matrix to agonize the trkA receptor (Maliartchouk et al., *Mol. Pharmacol.* 57:385-391, 2000). Other molecules such as adenosine or synthetic adenosine agonists (e.g., CGS 21680) can act through other receptors such as the adenosine 2A receptor to activate Trk receptors (Lee and Chao, *PNAS* 98:3555-3560, 2001). This interaction provides trophic support for the neural cells of the modified cochlear implant. Optionally, therapeutic agents such as analgesics, antibiotics, anti-inflammatories, steroids, and the like can also be included in the polymer mix.

The ECM proteins, neurotrophins and other factors for supporting cell growth can be immobilized on the polymer or gel and can interact with the cell receptors to encourage outgrowth, or to encourage differentiation of stem cells or stem cell-derived progenitor cells.

The polymer or gel mix, including biological cells, and optionally the ECM proteins and growth factors can be applied to an implant (e.g., used to coat the electrode bundle of the implant). Alternatively, the polymer or gel mix can be applied to the implant (e.g., to the electrode bundle) and the cells applied in a second step. Regardless of the order of application, the cells can be stem cells, progenitor cells, mature neurons, or a combination thereof.

The modified cochlear implant can also include one or more lumens or reservoirs that contain bioactive compounds or pharmaceutical compositions (e.g., to prevent bleeding, scarring) that can be released over time. This extra store of factors may facilitate an enhanced and enduring effect on neurite outgrowth, prevent neuron degeneration, and may help to optimize the overall health of the implant.

Cells. The neural cells and progenitor cells appropriate for attachment to a modified cochlear implant can be derived from stem cells. Stem cells are unspecialized cells capable of extensive proliferation. Stem cells are pluripotent and are believed to have the capacity to differentiate into most cell types in the body (Pedersen, *Scientif Am.* 280:68, 1999), including neural cells, muscle cells, blood cells, epithelial cells, skin cells, and cells of the inner ear (e.g., sensory cells, such as hair cells, and auditory nerve cells, such as spiral ganglion cells). Stem cells are capable of ongoing proliferation in vitro without differentiating. As they divide, they retain a normal karyotype, and they retain the capacity to differentiate to produce adult cell types. Stem cells can differentiate to varying degrees. For example, stem cells can form cell aggregates called embryoid bodies in hanging drop cultures. The embryoid bodies contain neural progenitor cells that can be selected by their expression of an early marker gene such as Sox1 and the nestin gene, which encodes an intermediate filament protein (Lee et al., *Nat. Biotech.* 18:675-9, 2000).

Stem cells useful for generating neural cells for growth on a cochlear implant can be derived from a mammal, such as from a human, mouse, rat, pig, sheep, goat, or non-human primate. If cells from a non-human mammal are applied to the modified cochlear implant, then an immunosuppressant will also be administered to prevent rejection. Exemplary immunosuppressants include antiproliferative agents (e.g., azathioprine, cyclophosphamide, and methotrexate); anti-inflammatory agents, such as corticosteroids (e.g., prednisone and prednisolone); and inhibitors of lymphocyte activation, such as cyclosporines (e.g., cyclosporine A, cyclosporine B, and cyclosporine G) and FK506. Other suitable immunosuppressive agents include statins, TGFβ1, uteroglobin, TH2 cytokine, rapamycin, mycophenylate and antibodies against adhesion molecules or T cell signaling molecules. For example, antibodies against the T cell signaling molecules B7 and CD28 are suitable immunosuppressive agents.

Stem cells can be derived from any number of tissues including, but not limited to, ear, eye, bone marrow, blood, or skin. For example, stem cells have been identified and isolated from the mouse utricular macula (Li et al., *Nature Medicine* 9:1293-1299, 2003). Stem cells useful for generating neural cells can be adult stem cells, and therefore derived from differentiated tissue, or the cells can be from embryonic tissue (called "embryonic stem cells" or "ES cells"). The stem cells can also be derived from umbilical cord fluid.

Methods of culturing neurons and neural progenitor cells for attachment to a cochlear implant include culturing stem cells under conditions that cause a stem cell to differentiate into a neural cell or progenitor neural cell (see below and, e.g., Lee et al., *Nat. Biotechnol.* 18:675-9, 2000). The cells derived from stem cells and applied to the cochlear implant need not be fully differentiated to be therapeutically useful. A partially differentiated cell that can further differentiate into a neural cell can be applied to the modified cochlear implants described herein. The cells applied to the modified cochlear implant need only to be differentiated enough, or have the capability to differentiate to an extent that allows them to convey information from the electrodes of the implant to the patient's auditory nervous system.

Neurons or neural progenitor cells can be generated from stem cells isolated from a human, such as from the intended recipient of the modified cochlear implant, or from a matched donor. A matched donor will have a compatible ABO blood type. A donor will preferably have identical or nearly identical human leukocyte antigens (HLAs) as the implant recipient (e.g., 6 of 6, or 5 of 6, or 4 of 6 of the donor's HLA profile will match the recipient's). Stem cells can be derived from embryonic tissue or from umbilical cord fluid, or stem cells can be derived from mature (e.g., adult) tissue, such as tissue from the inner ear, central nervous system, blood, skin, eye, bone marrow, or other accessible tissue. Any method for culturing stem cells and inducing differentiation into neural cells can be used.

A stem cell or progenitor cell can be isolated from the inner ear of an animal. These methods include providing tissue from the inner ear of the animal, where the tissue includes at least a portion of the utricular maculae. The animal can be a mammal, such as a mouse, rat, pig, rabbit, goat, horse, cow, dog, cat, primate, or human. The isolated tissue can be suspended in a neutral buffer, such as phosphate buffered saline (PBS), and subsequently exposed to a tissue-digesting enzyme (e.g., trypsin, leupeptin, chymotrypsin, and the like) or a combination of such enzymes, or a mechanical (e.g., physical) force, such as trituration, to break the tissue into smaller pieces. In one alternative, both mechanisms of tissue disruption are used. For example, the tissue can be incubated in a solution containing about 0.001-1.0% enzyme (e.g., about 0.001%, 0.01%, 0.03%, 0.05%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 μm or less, about 70 μm or less, about 60 μm or less, about 50 μm or less, about 40 μm or less, about 30 μm or less, about 35 μm or less, or about 20 μm or less. The cells can be frozen for future use or placed in culture for expansion or differentiation. The cells can be maintained on a feeder layer of cells. For example, embryonic stem cells can be maintained on a feeder layer of mitotically inactivated primary mouse embryonic fibroblasts, as described in Pirity et al. (*Methods Cell Biol.* 57:279-93, 1998). Optionally, a cytokine, such as LIF can be added to the maintenance medium.

The separated cells can be placed in individual wells of a culture dish at a low dilution and cultured to differentiate into cells having characteristics of cells of the inner ear or of neural cells. The cells can be distributed in the culture dish so that each dish, or a well therein, includes only a single cell. To initiate in vitro differentiation of embryonic stem cells in hanging drop cultures, the cells can be removed from the feeder layer and LIF. This can stimulate the formation of embryoid bodies in hanging drops. The cells can be allowed to differentiate to various stages. Thus, partially or more fully differentiated neural cells are useful for attachment to a cochlear implant. Formation of spheres (clonal floating colonies) from the isolated cells can be monitored, and the spheres can be amplified by disrupting them (e.g., by physical means) to separate the cells. These cells can be cultured again to form additional spheres. Further culturing of the cells in the absence of or in lower amounts of growth factors will induce the spheres (and the cells of the spheres) to differentiate further into more highly developed cells of the inner ear.

Appropriate stem cell culture medium is described in the art, such as in Li et al. (*Nat. Med.* 9:1293-1299, 2003). For example, stem cells can be cultured in serum free DMEM/high-glucose and F12 media (mixed 1:1), and supplemented with N2 and B27 solutions and growth factors. Growth factors such as EGF, IGF-1, and bFGF have been demonstrated to augment sphere formation in culture. In vitro, stem cells often show a distinct proliferation potential for forming spheres. Thus, the identification and isolation of spheres can aid in the process of isolating stem cells from mature tissue for use in making fully or partially differentiated neural cells. The growth medium for cultured stem cells can contain one or more or any combination of growth factors, provided that the stem cells do not differentiate. To induce the cells (and the cells of the spheres) to differentiate, the medium can be exchanged for medium lacking growth factors. For example, the medium can be serum-free DMEM/high glucose and F12 media (mixed 1:1) supplemented with N2 and B27 solutions. Equivalent alternative media and nutrients can also be used. Culture conditions can be optimized using methods known in the art.

The cells can be monitored for expression of cell-specific markers. Neuronal progenitor cell populations can be identified by expression of the marker protein nestin. Cells of the spiral ganglion can be identified by the expression of ephrinB2, ephrinB3, trkB, trkC, GATA3, BF1, FGF10, FGF3, CSP, GFAP, and Islet1. Expression of cell-specific markers can be assayed by traditional methods, including RT-PCR, Northern blot, Western blot, microarray analysis (Lockhart et al., *Nat Biotechnol* 14:1675-1680, 1996), and immunocytochemistry, which includes the staining of cells or tissues using an antibody against a specific antigen. Expression of these markers can be monitored before applying the cell to an implant. Differentiation into neural cell types can also be monitored by assaying for the development of neural cell morphology, an acquired negative resting potential, and the ability to fire action potentials. Resting potential and the ability to fire action potentials can be assayed by known methods, including extracellular single unit voltage recording, intracellular voltage recording, voltage clamping, patch clamping, voltage sensitive dyes, and ion sensitive electrodes.

In certain embodiments, the cells within a modified cochlear implant (e.g., cells on or in close proximity to the electrodes) can be modified by the induction of an exogenous vector that includes a nucleic acid sequence encoding polypeptide. For example, neural progenitor cells can be transfected with a vector for overexpressing an $\alpha_v\beta_3$ integrin. These cells would be expected to have an enhanced ability to extend neurites as this integrin has been shown to mediate neurite extension from ganglion neurons on laminin substrates (Aletsee et al., *Audiol. Neurootol.* 6:57-65, 2001). Neurite extension can also be enhanced by the addition of neurotrophins (e.g., BDNF, NT3 and LIF) (Gillespie et al., *NeuroReport* 12:275-279, 2001). A Sonic hedgehog (Shh) polypeptide or polypeptide fragment (e.g., Shh-N), can also be useful as an endogenous factor to enhance neurite extension. Shh is a developmental modulator for the inner ear and a chemoattractant for axons (Charron et al., *Cell* 113:11 23, 2003). The nucleic acid sequence encoding the polypeptide can be under the control of a promoter, such as a constitutive promoter (e.g., a CMV or human U6 promoter).

The stem cells, neural progenitor cells or differentiated neural cells can be added to the ECM or hydrogel coating before applying the coating to the modified cochlear implant, or the ECM or hydrogel coating can be applied to the implant and then the cells applied to the coating. The cells can be applied as separated cells, or cell aggregates, such as embryoid bodies.

Treatment methods. Treatment methods include implanting a modified cochlear implant into a subject who has a hearing loss. Use of the modified cochlear implant can improve the ability of the subject to hear.

A human having a hearing disorder can be fitted with a modified cochlear implant that includes cells. As noted, the cells can be attached to one or more electrodes or placed within the implant in close proximity to the electrodes. Upon successful implantation, processes will extend from the implant (e.g., from the electrodes) and will form synaptic connections with the auditory nerve, thereby stimulating the auditory nerve. The implants of the invention are not limited however, to those in which the cells form any particular connection or combination of connections. The cells within the implant may migrate or extend processes in a variety of ways to convey signals received from the implant or the external environment to the patient's nervous system in such a way that the patient experiences an improvement in the ability to hear.

Any human experiencing a hearing loss is a candidate recipient of a modified cochlear implant. A human having a hearing loss can hear less well than the average human being, or less well than on a prior occasion (e.g., less well than in years past or than before an injury). For example, hearing can be diminished by at least 5, 10, 30, 50% or more. The human can have mild hearing loss (e.g., difficulty hearing sounds below an intensity range of about 20 dB to 40 dB), moderate hearing loss (e.g., difficulty hearing sounds below an intensity range of about 40 dB to 60 dB), severe hearing loss (e.g., difficulty hearing sounds below an intensity range of about 60 dB to 80 dB) or profound hearing loss (e.g., difficulty hearing sounds below an intensity range of about 80 dB or higher). The human can have sensorineural hearing loss, which results from damage or malfunction of the sensory part (the cochlea) or the neural part (the auditory nerve) of the ear, or conductive hearing loss, which is caused by blockage or damage in the outer and/or middle ear. Alternatively, the human can have mixed hearing loss, which is caused by a deficit in both the conductive pathway (in the outer or middle ear) and in the nerve pathway (the inner ear). An example of a mixed hearing loss is a conductive loss due to a middle-ear infection combined with a sensorineural loss due to damage associated with aging. The human can have unilateral or bilateral hearing loss (loss of hearing in one or both ears, respectively). To merit the use of an implanted device, the loss of hearing in the human is likely to be so severe that a hearing aid does not improve hearing.

The devices, compositions, and methods described herein are appropriate for the treatment of hearing disorders resulting from sensorineural hair cell loss or auditory neuropathy. Humans with sensorineural hair cell loss experience the degeneration of cochlear hair cells, which frequently results in the loss of spiral ganglion neurons in regions of hair cell loss. Such humans may also experience loss of supporting cells in the organ of Corti, and degeneration of the limbus, spiral ligament, and stria vascularis in the temporal bone material. Humans with auditory neuropathy experience a loss of cochlear sensory neurons while the hair cells of the inner ear remain intact.

The subject can be deaf or have a hearing loss for any reason or as a result of any type of event. For example, a human can be deaf because of a genetic or congenital defect; for example, a human identified as a candidate for treatment can have been deaf since birth, or can be deaf or hard-of-hearing as a result of a gradual loss of hearing due to a genetic or congenital defect. In another example, a human identified as a candidate for treatment can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss. A human can experience chemical-induced ototoxicity, wherein ototoxins include therapeutic drugs including antineoplastic or chemotherapeutic agents, salicylates, quinines, and aminoglycoside antibiotics, contaminants in foods or medicinals, and environmental or industrial pollutants. A human can have a hearing disorder that results from aging or that is associated with a disease or disorder such as Mèniéré's disease, multiple sclerosis, a brain tumor or a stroke.

Candidate recipients of the modified cochlear implants described herein can be any age including children (e.g., children about 12 months through 18 years) and adults over 18 years of age. The modified cochlear implants may be especially beneficial to hearing—impaired children between the ages of two and three, as it is around this age that language skills develop the fastest.

A modified cochlear implant including attached cells can be implanted in a human by any method known in the art. For example, implantation can be performed under general anesthesia. Generally, an incision is made behind the ear to expose the mastoid bone, which is then removed to allow identification of the facial nerve and the cochlea. An opening is then created in the cochlea to allow insertion of the electrode array including the attached cells. An insertion tool, or stylet, may be used to facilitate placement of the electrode array inside the cochlea. To secure the implanted processor and to reduce the prominence of the processor on the side of the head, a bony depression can be drilled in the designated position of the internal processor (typically above and behind the outer ear). A permanent suture, Gortex sheeting, or any of a variety of other means known in the field of cochlear implantation can be used to secure the device into position. The skin incision can then be closed using sutures, such as absorbable sutures, and a compression/protective head wrap can be applied for 1, 2, or 3 days or more to allow time for the skin incision to heal. The initial activation of the implant may be delayed from 2, 3, 4, 5, or 6 weeks or more after surgery, to allow more time for recovery. The electrodes may be activated in small batches, such that activation of all the electrodes will occur over a period of several days or weeks. A period of rehabilitation may follow activation of the electrodes to build hearing, speech and language skills. Rehabilitation sessions may occur weekly, bimonthly, monthly or periodically over the course of up to a year or more. The rehabilitation regimen can be maintained for 5 months, 6 months, 8 months, one year, or longer.

Before and after implantation of the modified cochlear implant, and throughout a course of rehabilitation, the human can be tested for an improvement in hearing. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Brainstem evoked response audiometry (BERA or ABR) can also be performed. In BERA, sounds are placed in the ear, and the brainstem's response is recorded from electrodes taped to the patient's head. Electrocochleography can be used to provide information about the functioning of the cochlea and the first part of the nerve pathway to the brain.

The efficacy of the treatment methods described herein can be assayed by determining an improvement in the subject's ability to hear. Alternatively, efficacy can be assayed by measuring distortion product otoacoustic emissions (DPOAEs) or compound action potential (CAP). A patient is successfully treated upon experiencing any objective or subjective improvement in their hearing.

Certain imaging techniques can be used to supplement the hearing tests. These include angiography, and magnetic resonance angiography (MRA) in particular, to produce images of the blood vessels to the brain, and SPECT or PET scans, which produce images of microscopic blood flow within the brain.

Supplemental Therapies. Treatment with a modified cochlear implant can be supplemented with the administration of cells (e.g., stem cells, partially differentiated progenitor cells, or more differentiated neural cells) that are not attached to the implant. These cells can be generated by the methods described herein. For example, the cells can be transplanted, (e.g., in the form of a cell suspension) into the ear by injection. For example, the cells can be injected or otherwise placed into the luminae of the cochlea. Injection can be, for example, through the round window of the ear or through the bony capsule surrounding the cochlea. The cells can be injected through the round window into the auditory nerve trunk in the internal auditory meatus or into the scala tympani. The cells can be implanted near the junction between the cochlea and the brainstem. Alternatively, or in addition, the cells can be implanted within the cochlea, such as within the scala tympani, within the scala vestibuli, within the scala media, within the modiolus, or within Rosenthal's canal.

To improve the ability of the cell to engraft, the supplemental biological cells can be modified prior to differentiation. For example, the cells can be engineered to overexpress one or more anti-apoptotic genes in the progenitor or differentiated neural cells. The FAK tyrosine kinase or Akt genes are candidate anti-apoptotic genes that can be useful for this purpose; overexpression of FAK or Akt can prevent cell death in spiral ganglion cells and encourage engraftment when transplanted into another tissue, such as an explanted Organ of Corti (see for example, Mangi et al., *Nat. Med.* 9:1195-1201, 2003).

Supplemental cells implanted into the ear of the implant recipient can form neurites that extend towards the brainstem and can also form neurites that extend towards the electrode of the cochlear implant. Neurotrophic factors within the matrix applied to the electrodes of the implant or in releasable form in a chamber in the cochlear implant can encourage the extension of neurites towards the electrodes. For example, neurotrophins such as BDNF, NT3, and leukemia inhibitory factor (LIF) included in the matrix applied to the electrodes of the cochlear implant can enhance the extension of neurites from the supplemental implanted cells towards the electrodes where they can synapse with cells of the modified cochlear implant. Sonic hedgehog (Shh) polypeptides or polypeptide fragments (e.g., the N-terminus of Shh, Shh-N) included in the matrix of the modified cochlear implant can also stimulate the extension of neurites towards the electrodes of the implant. Shh is a developmental modulator for the inner ear and a chemoattractant for axons (Charron et al., *Cell* 113:11-23, 2000).

Treatment methods can also include administration of a composition to the ear to encourage neural cell outgrowth from the cochlear implant or to inhibit degeneration of the implant-associated neural cells. These compositions can be the same as or unique from those described above and associated with the implant. For example, pharmaceutical compositions can include one or more factors to enhance neural cell survival, migration, or process extension, such as neurotrophins (e.g., BDNF, NT3, or LIF), or a chemoattractant such as an Shh polypeptide or polypeptide fragment (e.g., Shh-N).

A supplemental composition (i.e., a composition administered in connection with the modified implant but not physically associated with it) can include a steroid, a molecule to promote healing or inhibit bleeding, inflammation, or scar tissue formation.

The compositions of the invention, whether combined with cells and used in connection with the implant or administered separately can contain a carrier, many of which are known to skilled artisans. Carriers that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, and glycerol. Where a composition is administered independently from the implant, it can be administered by any route of administration. For example, liquid solutions can be made for administration by injection into the ear. Methods for making such formulations can be found in, for example, *Reming-* ton's *Pharmaceutical Sciences*, 18th Ed., Gennaro, ed., Mack Publishing Co., Easton, Pa., 1990.

The pharmaceutical compositions and methods described herein can be used independently or in combination with one another to supplement treatment with a modified cochlear implant. That is, subjects can be administered one or more of the pharmaceutical compositions in temporally overlapping or non-overlapping regimens. The subject can also be administered a solution or tissue containing the differentiated neural cells or stem-cell derived progenitor cells described above. When therapies overlap temporally, the therapies may generally occur in any order and can be simultaneous or interspersed. Administration of a pharmaceutical composition in addition to treatment with a modified cochlear implant is optional. Treatment of hearing loss may consist solely of administration of a modified cochlear implant as described herein.

The formulations and routes of administration can be tailored to the specific hearing disorder being treated, and for the specific human being treated. For example, the human can have been deaf from birth due to a genetic or environmental event, or a child or adult human can be losing hearing due to environmental factors such as prolonged exposure to loud noises, or a human can be experiencing a hearing loss due to aging. Therefore the human can be any age (e.g., an infant or an elderly person), and formulation and route of administration can be adjusted accordingly. A subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

Generally the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: *Remington's Pharmaceutical Sciences*, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: *Goodman & Gilman's The Pharmacological Basis of Therapeutics*, 9th Ed., Hardman et al., eds., McGraw-Hill, New York, N.Y., 1996).

A pharmaceutical composition as described herein can be packaged and labeled for use in conjunction with a modified cochlear implant for treatment of a hearing disorder.

Pharmaceutical compositions can be formulated in a conventional manner using one or more physiologically acceptable carriers or excipients. For example, a composition can be formulated for administration by drops into the ear, insufflation (such as into the ear), topical, or oral administration.

In another mode of administration, the composition can be directly administered in situ to the cochlea of the inner ear, such as via a catheter or pump. A catheter or pump can, for example, direct a differentiation agent into the cochlear luminae or the round window of the ear.

In another route of administration, a differentiation agent can be injected into the ear, such as into the luminae of the cochlea (e.g., the Scala media, Sc vestibulae, and Sc tympani). Injection can be, for example, through the round window of the ear or through the cochlear capsule.

The invention is further illustrated by the following examples, which should not be construed as further limiting.

EXAMPLES

Example 1

Neurons were Isolated from the Inner Ear of a Pig Fetus for use in Transplantation Studies We isolated pig fetal spiral ganglion cells from the inner ear after timed pregnancies and placed the cells in culture for periods up to two weeks. Gestational ages of E36, E41, E49, E60 and E63 were compared. Following isolation of whole cochlea, the tissues containing spiral ganglion cells were separated from other tissues and incubated with trypsin-EDTA at 37° C. for 10 minutes. After three washes with PBS plus DNAse, tissues were triturated with three pre-calibrated flame polished Pasteur pipettes with progressively smaller apertures. Cells were resuspended in PBS plus glucose solution at approximately $1 \times 10^8$/ml. The viability of the cells was determined by trypan blue exclusion assay prior to transplantation. Some cells were plated on poly-D lysine-coated 12-well culture plates in complete neurobasal medium.

Immunohistochemical staining revealed that the E36 neurons did not express neurofilament but did express neuron specific enolase. At days E49 and later, the neurons expressed neuron specific enolase and neurofilament as well as galactocerebrosidase. The later time points yielded an increased ratio of connective tissue components relative to neurons. The best yield of cells was at E41, and these cells could be stained with all three of the markers. This time point was therefore selected for the isolation of cells for transplantation.

Example 2

Embryonic Stem Cell Cultures were Established and Controlled Differentiation of Different Cell Types was Observed We established cultures of the murine ES cell lines YC5/EYFP, a derivative of the totipotent cell line R1 (Nagy et al., *Proc. Natl. Acad. Sci. USA* 90:8424-8, 1993); ROSA26-6; and Sox1-GFP (Aubert et al., *Nat. Biotechnol.* 20:1240-5, 2002). YC5/EYFP cells carry the gene for enhanced yellow fluorescent protein (EYFP) under control of a promoter composed of a cytomegalovirus (CMV) immediate early enhancer coupled to the β-actin promoter (Hadjantonakis et al., *Mech. Dev.* 76:79-90, 1998). ROSA26-6 cells and their derivatives express the lacZ gene encoding the bacterial beta-galactosidase enzyme (Pirity et al., *Methods Cell Biol.* 57:279-93, 1998). The Sox1-GFP cells express GFP controlled by the promoter for the early neural marker Sox1.

Low passage ES cells are maintained on a feeder layer of mitotically inactivated primary mouse embryonic fibroblasts (Pirity et al., *Methods Cell Biol.* 57:279-93, 1998). Undifferentiated ES cells proliferate actively and form compact clusters of small cells. We initiated in vitro differentiation of ES cells in hanging drop cultures in the absence of embryonic fibroblast feeder cells and of leukemia inhibitory factor (LIF), a cytokine that promotes the pluripotency of ES cells. Within two days, cell aggregates of uniform size termed embryoid bodies form in the hanging drops.

Using a published protocol (Lee et al., *Nat. Biotechnol.* 18:675-9, 2000), we were able to select neural progenitor cell populations that express the defining marker protein nestin. Nestin-positive progenitors were subjected to in vitro differentiation conditions (see Lee et al., *Nat. Biotechnol.* 18:675-9, 2000) that led to differentiation of astrocytes and neurons.

Using protocols for the selection of progenitor cells, we were able to select inner ear progenitor cells that express a variety of marker genes indicative of the developing inner ear. In particular, we found after selection from embryoid body-derived cells, cell populations that expressed genes indicative of the otic placode, such as Pax2, BMP4, and BMP7 (Morsli et al., *J. Neurosci.* 18:3327-35, 1998; Groves and Bronner-Fraser, *Development* 127:3489-99, 2000). In addition, we found expression of marker genes for the developing sensory epithelia (for example, Math1 (Bermingham et al., *Science* 284:1837-41, 1999), delta1, jagged1 and jagged2 (Lanford et al., *Nat. Genet.* 21:289-92, 1999; Morrison et al., *Mech. Dev.* 84:169-72, 1999)). Gene expression was detected by reverse transcription followed by polymerase chain reaction (RT-PCR). The differentiated cells were analyzed 14 days after the removal of bFGF from the culture. The expression of the marker genes correlated with the developmental stage of the progenitor or mature cells as nestin and Pax2 and BMP7 expression decreased upon differentiation of the cells and appearance of hair cell markers.

Hair cell markers in differentiated cells were also detected by immunohistochemistry. The hair cells produced in this system co-expressed markers important for hair cell differentiation (Math1) and survival (Brn3.1) and markers present in the more fully differentiated cells (myosin VIIa).

In preliminary experiments, we explored whether it was feasible to isolate clonal lines that represent hair cell and neural progenitors from embryoid bodies. We were able to generate spheres that contained progenitors, which we identified by expression of the early neural marker Sox1 and the intermediate filament protein nestin. We were able to propagate these progenitor cells in serum-free conditions for more than three months either in the form of spheres or as adherent cultures in the presence of mitogenic growth factors. We routinely observed differentiation of the progenitor cells after removal of growth factors in adherent cultures.

Example 3

Different Neural Progenitor Cells were Generated from ES Cells

We determined that it was feasible to use embryoid bodies to isolate clonal lines that represent neural progenitors. One goal of the project was to generate neurons with different features that could be used to generate neural populations having characteristics similar to spiral ganglion neurons. The principal idea of this technique was to use the sphere-forming capacity of neural stem cells to clone different cell lines. Our initial results indicated that we were able, for example, to generate spheres that contain neural progenitors, which we identified by expression of the early neural marker Sox1 and the intermediate filament protein nestin.

We were able to propagate these neural progenitor cells in serum-free conditions for more than three months either as spheres or as adherent cultures in the presence of mitogenic growth factors. We routinely observed neural differentiation of the progenitor cells either in aging spheres or after removal of growth factors in adherent cultures. In experiments done with Sox1-GFP ES cells, we were able to generate proliferating neural progenitor lines that expressed nestin and Sox1, visible in real-time by green fluorescence. These cells readily differentiated into morphologically and immunologically distinct neurons after removal of mitogenic growth factors.

We examined the electrophysiological properties of neurons generated from embryonic stem cells and from stem cells harvested from adult ears. Using the strategy outlined above we examined embryonic stem cells differentiated to become presumptive auditory sensory neurons. The cells adopted neural morphology and acquired negative resting potentials and the ability to fire action potentials.

Example 4

Development of an Assay for Differentiation of ES Cells

In order to more systematically test the effects of different genes or compounds on the conversion of ES cells to cells resembling spiral ganglion neurons, we developed a luciferase assay system in which the conversion of the progenitors to the desired cell types is readily detected by a reporter construct. The aim was to have the reporter construct under the control of a promoter that is activated in the differentiated cell but is inactive in the progenitor cells, so that a luciferase signal is generated by differentiation of the cells. The assay can be performed using conditions known to be useful for generating neurons from ES cells. Cells that are grown in the presence of growth factors are cultured in medium without growth factors, and this induces their differentiation to neurons based on the expression of markers. Under these conditions, the reporter cells will differentiate and generate a signal. We used mouse ES cells (ROSA 26) to generate neural progenitors in the presence of EGF, IGF-1 and bFGF. The neural progenitors were used for construction of the reporter cell lines. The progenitor cells were positive for nestin expression and were kept in culture in the presence of bFGF.

To determine whether a cell-specific promoter could be measured in this assay, neural progenitors were co-transfected with the firefly luciferase gene controlled by a GFAP promoter and a vector that contains the Renilla luciferase gene under control of a CMV promoter. The firefly luciferase construct was made in the pGL3 basic vector (Promega, Madison, Wis.) that contains the firefly luciferase gene and a multiple cloning site for the promoter. The GFAP promoter inserted into this site allowed us to measure the activity of this promoter relative to the constitutively active control promoter in a separate vector driving the Renilla luciferase. Co-transfection of the vectors into the neural progenitors followed by lysis of the cells and measurement of luciferase activity (using two substrates for measurement of firefly and Renilla luciferase) allowed us to demonstrate that the neural progenitors were initially negative for GFAP expression but after removing bFGF from the culture medium, had increasing amounts of luciferase activity (at 24, 48 and 72 hours). Furthermore, the neural progenitor cells expressed the Renilla and firefly luciferases at levels that were proportional to the amount of vector used for transfection. These results indicate that the assay is useful for determining quantitative effects relating to the differentiation of the cells in response to individual genes or factors.

Example 5

ES Cell-Derived Progenitors were Grafted into a Developing Chicken Inner Ear We established microsurgical techniques to manipulate developing chicken ears. For injection of ES cell-derived progenitors, we used beveled glass-capillary micropipettes for injections into the otic pits or vesicles of stage 10-16 chicken embryos (1.5-2.5 days of embryonic development, (Hamburger and Hamilton, *J. Morphol.* 88:49-92, 1951)). Genetically labeled ES cell-derived inner ear progenitors were implanted into the inner ear of chicken embryos and their fate was followed through early otic development. The cells were observed to be engrafted into a preexisting epithelium and certain criteria were identified as being necessary for the cells to engraft. Progenitor cells only survived when implanted as cell aggregates. Progenitor cells that were injected into the otic vesicle in the form of suspensions were not traceable. Integration of cells from the progenitor cell aggregates into the epithelial layers that form the otic vesicle occurred preferentially at sites of epithelial damage. The progenitor-derived cells were incorporated throughout the inner ear, but in our study, we only focused on hair cell development. Murine cells only upregulated hair cell markers when situated in a developing sensory epithelium and only when they were located on the luminal site of the epithelium—in the correct orientation for hair cells. Progenitor-derived cells that we found elsewhere in the inner ear did not display expression of hair cell markers.

In addition to the repopulation of the sensory epithelium (Li et al., *Proc. Natl. Acad. Sci. USA* 100:13495-500, 2003), we also found progenitor cell derivatives outside of the sensory epithelia in the auditory ganglion. In fact, we initially observed more efficient integration of cells into the auditory ganglion than into the cochlear sensory epithelium.

Example 6

Transplantation-Repair Studies in the De-Afferented Cat

A unilaterally de-afferented cat is a useful animal model for the study of sensorineural hearing loss with either primary neural degeneration or primary hair cell damage followed by secondary neural degeneration. We cut the auditory nerve in cats and allowed them to survive for up to 1 year post surgery. Such surgery can result in near complete loss of the auditory nerve, yet all other structures of the cochlea remain normal. Months after nerve section, there appeared to be a reinnervation of the organ of Corti by branches of the facial nerve, which can be seen, in serial sections, streaming through the ganglion without a soma. Within the organ of Corti, this reinnervation appeared as spiraling fibers lining either side of the inner hair cell. These results suggested (i) that hair cells can survive in the adult ear without their afferent innervation, and (ii) that the surviving hair cells are likely expressing signals that remain capable of attracting new neural contacts.

Figure 3A:
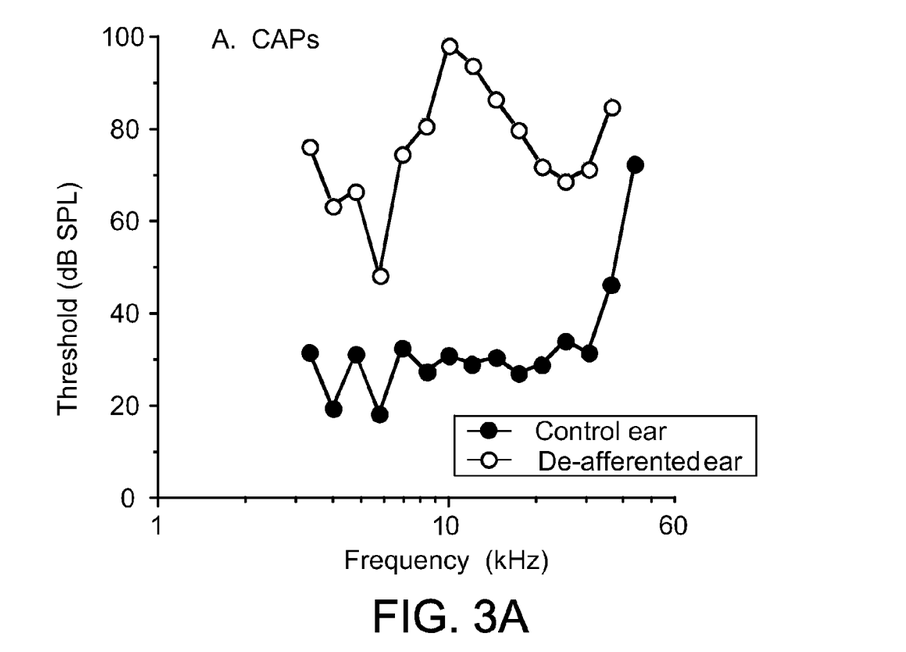
FIG. 3A is a graph illustrating the compound action potential (CAP) threshold elevation in de-afferented and control cat ears. The auditory nerve was cut 10 weeks prior to taking the measurements.
Figure 3B:
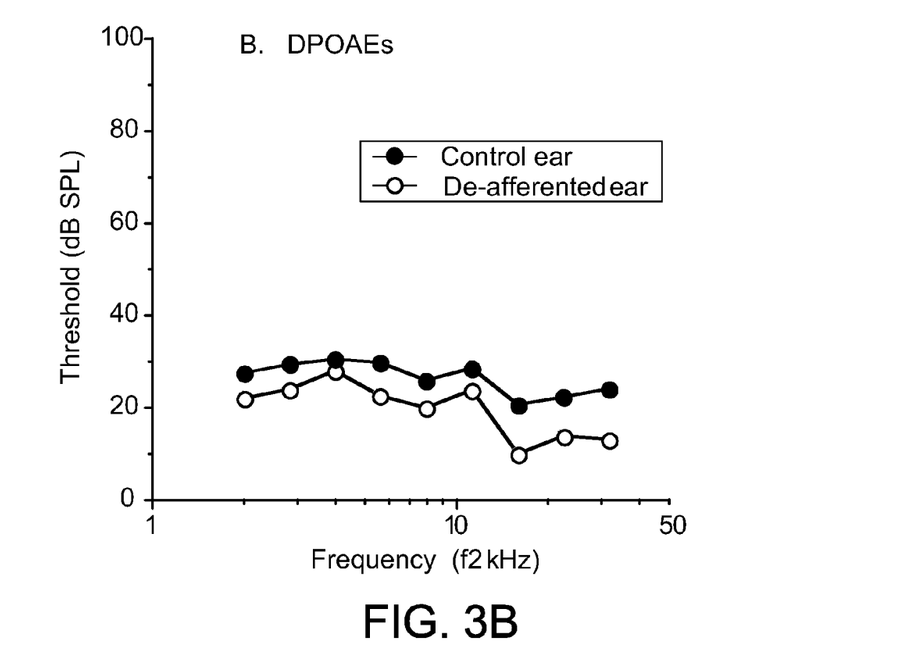
FIG. 3B is a graph illustrating the distortion product otoacoustic emissions (DPOAEs) in the de-afferented and control cat ears. The auditory nerve was cut 10 weeks prior to taking these measurements.

This animal model was used as a platform for neural transplantation studies. As shown in FIGS. 3A and 3B, the distortion product otoacoustic emissions (DPOAEs) remained normal in the de-afferented ear, while there was a dramatic elevation of compound action potential (CAP) thresholds in the de-afferented ear. These results indicated that all the processes underlying transduction and amplification in the cochlea were normal in the de-afferented ear. Therefore, this model system is ideally suited to a neural transplantation experiment.

We have performed a number of xenotransplantation experiments in the unilaterally de-afferented cat and assessed the extent of incorporation and differentiation of progenitor cells up to 8 weeks post transplantation. The basic approach in the eight animals studied to date has been to (1) cut the auditory nerve bundle near the Schwann glial border, (2) put the animals on cyclosporin immunosuppression therapy, (3) inject neural progenitor cells after a variable recovery interval from 0 to 12 weeks, (4) allow a post-implantation survival of 1-8 weeks, (5) assess functional recovery via a terminal electrophysiological session, and (6) harvest the cochlea and the brain for histological verification of the extent of the primary neural degeneration and the survival and differentiation of transplanted cells.

The progenitor cells injected have included (i) immature spiral ganglion neurons isolated from fetal pigs and (ii) mouse ES cells, each expressing β-galactosidase reporters. In some cases, the exogenous cells were transplanted into the round window and in other cases into the auditory nerve, just peripheral to the site of the surgical section.

In one study, ES cells were transplanted into the auditory nerve four weeks after surgery. Functional recovery was assessed via a terminal electrophysiological session, and when the animal was sacrificed six weeks after transplantation, β-galactosidase positive cells were seen only in the vicinity of the electrode track (none were seen anywhere else in the nerve or cochlear nucleus). Some of these cells had neural morphology. In one case, a total of 150 β-gal positive cells were seen near the electrode track.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus for alleviating hearing loss caused by loss of hair cells and sensory neurons, the apparatus comprising:
    a cochlear implant comprising
        an electrode and
        a neural progenitor cell that is operably associated with the electrode to transmit electrical signals from the electrode to an auditory nerve, wherein the cell expresses nestin.

2. The apparatus of claim 1, wherein neural progenitor cell is obtained from a stem cell.

3. The apparatus of claim 2, wherein the stem cell is an adult stem cell or an embryonic stem cell.

4. The apparatus of claim 1, further comprising a holding area comprising additional neural progenitor cells.

5. The apparatus of claim 4, wherein the additional neural progenitor cells are obtained from stem cells.

6. The apparatus of claim 1, wherein the neural progenitor cell or the electrode with which it is operably associated is at least partially covered by a composition comprising a component of an extracellular matrix (ECM).

7. The apparatus of claim 6, wherein the component of the ECM is fibronectin, laminin, collagen, elastin, vitronectin, a proteoglycan, or a glycosaminoglycan.

8. The apparatus of claim 1, wherein the neural progenitor cell or the electrode with which it is operably associated is at least partially covered by a composition comprising a cytokine.

9. The apparatus of claim 8, wherein the cytokine is growth factor or chemokine that improves the survival, motility, or differentiation of the neural progenitor cell.

10. The apparatus of claim 9, wherein the growth factor is nerve growth factor (NGF), brain-derived neurotrophic factor (BDNF), neurotrophin-3(NT-3), ciliary neurotrophic factor (CNTF), neurotrophin-4/5 (NT-4/5), glial-cell line derived neurotrophic factor, leukemia inhibitory factor (LIF), or a fibroblast growth factor (FGF).

11. The apparatus of claim 1, wherein the neural progenitor cell or the electrode with which it is operably associated is at least partially covered by hydrogel or a composition comprising a polymer.

12. The method of claim 1, wherein the neural progenitor cells also express Sox1.

13. A method of treating a human patient who has sensorineural hearing loss, the method comprising:
providing a population of neural progenitor cells that express nestin;
applying the selected neural progenitor cells to an electrode on a cochlear implant; and
implanting the cochlear implant in the human, such that the neural progenitor cells differentiate into neurons and transmit an electrical signal from the implant to a cell within the patient's nervous system,
thereby improving the patient's hearing.

14. The method of claim 13, wherein the hearing loss is not significantly improved by the use of an external hearing aid.

15. The method of claim 13, wherein the hearing loss is severe or profound.

16. The method of claim 13, wherein the human patient is a child between the ages of about 12 months and 48 months.

17. The method of claim 13, wherein the human patient is an elderly patient.

18. The method of claim 13, wherein the method further comprises, prior to implanting the cochlear implant, the step of identifying a human patient in need of treatment.

19. The method of claim 13, wherein the method further comprises administering to the human patient a pharmaceutical composition comprising an active ingredient that serves as an analgesic, antibiotic, or anti-inflammatory agent.

20. The method of claim 13, wherein the method further comprises administering to the human patient a stem cell, a neural progenitor cell or a neuron, wherein the stem cell, neural progenitor cell or neuron is administered to the ear containing the cochlear implant, and the stem cell, neural progenitor cell or neuron is not associated with an apparatus of claim 1.

21. The method of claim 20, wherein the stem cell is an embryonic stem cell.

22. The method of claim 13 wherein the selected neural progenitor cells are applied to the electrode prior to implanting the cochlear implant in the human.

23. The method of claim 13, wherein the neural progenitor cells also express Sox1.

24. The method of claim 13 further comprising at least partially coating the electrode with a porous medium for hosting the neural progenitor cells.

25. The method of claim 24, wherein the porous medium comprises an additional bioactive compound that promotes neurite outgrowth from the neural progenitor cells.

26. The method of claim 25, wherein the bioactive compound comprises a neurotrophin.

* * * * *

UNITED STATES PATENT AND TRADEMARK OFFICE
CERTIFICATE OF CORRECTION

PATENT NO. : 9,265,933 B2
APPLICATION NO. : 11/518099
DATED : February 23, 2016
INVENTOR(S) : Albert Edge and Stefan Heller Page 1 of 1

It is certified that error appears in the above-identified patent and that said Letters Patent is hereby corrected as shown below:

In the claims,

In column 20, line 53, Claim 2, after "wherein" insert -- the --;

In column 21, line 10 (approx.), Claim 10, delete "neurotrophin-3(NT-3)," and insert -- neurotrophin-3 (NT-3), --, therefor;

In column 21, line 18 (approx.), Claim 12, delete "The method," and insert -- The apparatus --, therefor;

In column 22, line 17 (approx.), Claim 20, delete "an" and insert -- the --.

Signed and Sealed this
Twenty-fourth Day of May, 2016

Michelle K. Lee
*Director of the United States Patent and Trademark Office*